United States Patent [19]

Chabrol et al.

[11] Patent Number: 5,480,683

[45] Date of Patent: Jan. 2, 1996

[54] PROCESS FOR REDUCING THE COEFFICIENT OF FRICTION AND WEAR BETWEEN A METAL PART AND AN ORGANIC POLYMER-OR COPOLYMER-BASED PART AND ITS APPLICATION TO ARTIFICIAL LIMB-JOINTS AND FITTINGS WORKING IN MARINE ENVIRONMENTS

[75] Inventors: Claude Chabrol, Villeurbanne; Marc Robelet, Unieux; Robert Leveque, Firminy; Anne L. M. Pichat née Nedelec; Jean F. E. Rieu, both of St Etienne; Louis M. Rabbe, Fraisses; Andre Rambert, Lyons, all of France

[73] Assignee: Nitruvid, Argenteuil, France

[21] Appl. No.: 167,111

[22] Filed: Dec. 16, 1993

Related U.S. Application Data

[63] Continuation of Ser. No. 19,332, Feb. 17, 1993, abandoned, which is a continuation of Ser. No. 356,305, May 24, 1989, abandoned.

[30] Foreign Application Priority Data

May 24, 1988 [FR] France ..................... 88 06890

[51] Int. Cl.$^6$ ........................ B05D 3/06
[52] U.S. Cl. .................. 427/525; 427/2.26; 623/901
[58] Field of Search .............. 427/2, 523, 525, 427/528, 2.26, 2.27; 623/901, 18; 250/492.3

[56] References Cited

U.S. PATENT DOCUMENTS

| | | | |
|---|---|---|---|
| 4,107,350 | 8/1978 | Berg et al. | 427/38 |
| 4,452,827 | 6/1984 | Kolev et al. | 427/525 |
| 4,743,493 | 5/1988 | Sioshansi et al. | 427/525 |
| 4,764,394 | 8/1988 | Conrad | 427/38 |
| 4,872,922 | 10/1989 | Bunker et al. | 204/192.31 |
| 4,917,702 | 4/1990 | Scheicher et al. | 501/1 |
| 4,917,953 | 4/1990 | Hioki et al. | 427/38 |

FOREIGN PATENT DOCUMENTS

| | | |
|---|---|---|
| 2478113 | 9/1981 | France . |

OTHER PUBLICATIONS

Pichat, Rieu, Charbol, Rambert, "Effect of Ionic Implantation on the Resistance to Wear and Fatigue of Materials for Orthopaedic Use" Int. Symposium on wear–resistant materials, Bulletin du Cercle d'Etude des Metaux, 1987, 15–14, pp. 9–1.

Chabrol and Leveque, "Applications de l'implantation ionique dans le domaine de l'industrie mecanique, Memoires et Etudes Scientifiques Rayue de Metallurgic", Janvier 1983, pp. 43–54 (See English abstract p. 44).

G.R.E.C.O. Ives Journees Scientifiques Du Greco, Le Mont Saint Michel, 10 et 11 Jun. 1983, Le Polyethylene En Orthopedic, pp. 22–63.

Black, "The Future of Polyethylene", Editorials and Annotations, vol. 60–8, No. 3, Aug. 1978, pp. 303–306.

Picraux et al., "Ion Implantation of Surfaces", Scientific American, vol. 252, No. 3, 1985, pp. 102–113.

English Abstract of French Patent 2,478,113 published Sep. 1981.

Shioshansi, "Ion Beam Modification of Materials for Industry", Thin Solid Films, vol. 118, 1984, pp. 61–71.

Basta, Ion–Beam Implantation, "High Technology", Feb. 1985, pp. not numbered.

Chemical Abstracts, vol. 104, No. 12, Mar. 24, 1986, p. 442, No. 95419W, Columbis, Ohio US, F. Mathews et al., Enhanceent of the Tl–6A1–4V/Uhmwpe "Wear Couple Through Nitrogen Ion Implantation", Biomed Eng. Recent Dev. Proc. South, Biomed. Eng. Conf. 4th 1985 pp. 18–21.

Applied Optics, vol. 19, No. 18, Sep. 1, 1980, pp. 3022–3026, Optical Society of America, New York, US; E. Spiller et al., "Graded–Index AR Surfaces Produced Ion Implantation on Plastic Materials", Tab. I.

Picraux, S. and P. Peerey, "Ion Implantation of Surfaces", Scientific American, vol. 252, No. 3 (1985) pp. 102–113.

Shioshansi, P., "Ion Beam Modification of Materials for Industry", Thin Solid Films, vol. 118 (1984) pp. 61–71.

Basta, N., "Ion–Beam Implantation", High Technology, (Feb. 1985) pages not numbered.

Sioshansi, P., "Application Examples of the Surface Modification of Metals, Ceramics and Polymers by Ion Implantation", Kinzoku Hyomen Gijutsu, 39 (10), 1988, pp. 664–668.

*Primary Examiner*—Terry J. Owens
*Attorney, Agent, or Firm*—Cushman, Darby & Cushman

[57] ABSTRACT

A process for reducing the coefficient of friction and the wear between a metal part and an organic polymer- or copolymer-based part, in an aqueous medium containing chlorides, characterized in that the organic polymer- or copolymer-based part is submitted to a surface treatment by ionic implantation of elements selected from nitrogen, argon, oxygen and carbon.

5 Claims, 2 Drawing Sheets

PROCESS FOR REDUCING THE COEFFICIENT OF FRICTION AND WEAR BETWEEN A METAL PART AND AN ORGANIC POLYMER-OR COPOLYMER-BASED PART AND ITS APPLICATION TO ARTIFICIAL LIMB-JOINTS AND FITTINGS WORKING IN MARINE ENVIRONMENTS

This is a continuation of Application No. 08/019,332, filed on Feb. 17, 1993, now abandoned; which is a continuation of Appln. No. 07/356,305 filed May 24, 1989, now abandoned.

The present invention relates to a process for reducing the coefficient of friction and the wear between a metal part and an organic polymer- or copolymer-based part and is used for artificial limb-joints and for fittings working in marine environments.

Artificial limb-joints or rotating or sliding fittings generally include two parts which rub against each other. Generally, at least one of these parts is metal. The other is of polymer or is covered with an organic polymer- or copolymer-based layer. The resistance to friction and to wear of the couple is acceptable but could be improved by suitable surface treatments.

Polyethylene is in general used as the polymer. The metals used are generally stainless steels, or cobalt- or titanium-based alloys. In place of metals, other materials can also be used (ceramics, composites such as carbon-carbon, etc.).

The present invention aims to provide a process which allows in particular the reduction of friction and the wear between such parts functioning in an aqueous environment containing chlorides such as a physiological fluid or a marine environment.

The invention is described with reference to the drawings.

DETAILED DESCRIPTION OF INVENTION

Figure 1:
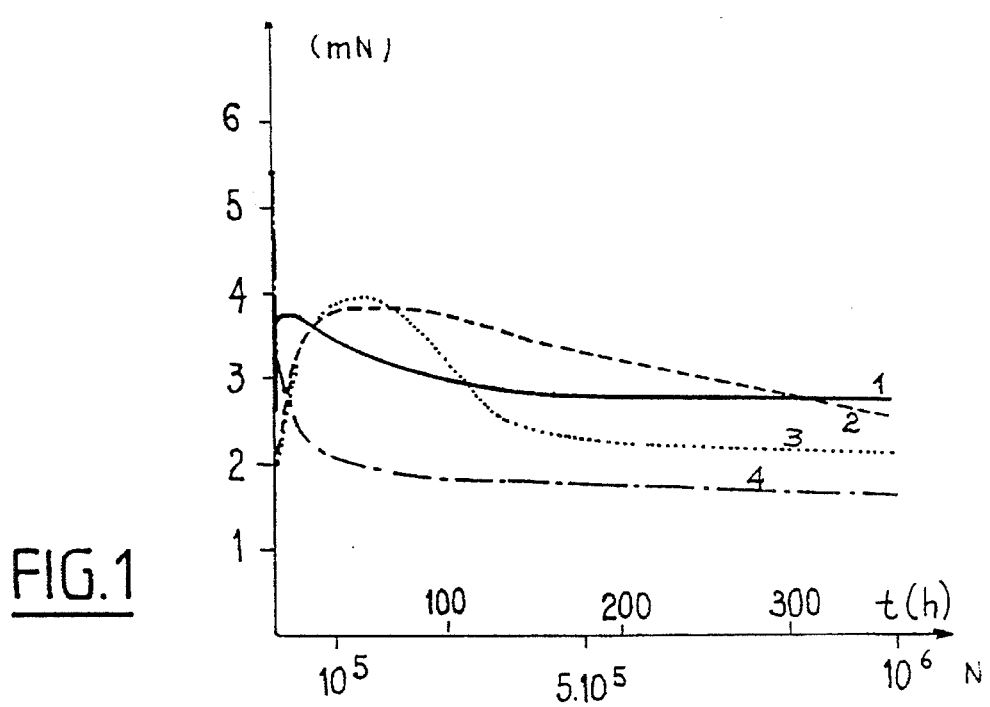
FIG. 1 is a graph of torque versus number of test cycles for various materials.

The subject of the present invention is a process for reducing the coefficient of friction and the wear between a metal part and an organic polymer- or copolymer-based part, in an aqueous medium containing chlorides, characterized in that the organic polymer- or copolymer-based part is submitted to a surface treatment by ionic implantation.

The present invention can be applied in particular when the polymer is a polyethylene, such as a high-density polyethylene, and with e very high molecular weight, but other polymers can be used: low-density polymers, reinforced polymers (fibres, particles . . .), etc.

The principle of ionic implantation consists of ionizing at least one atomic type chosen from nitrogen, argon, oxygen, carbon or other, then of accelerating it in an electric field at energies of to 500 keV, preferably 10 to 300 keV and even more advantageously 50 to 150 keV.

The operation is usually carried out under pressures of $10^{-2}$ to $10^{-4}$ Pa. Under these conditions, the ions penetrate into the polymer- or copolymer-based layer to a depth which can extend to several microns.

The implantation dose is usually $10^{12}$ to $10^{17}$ ions/cm$^2$.

The account of the following tests highlights the improvement obtained by using the process according to the invention.

1) Ionic implantation of high-density polyethylene with a very high molecular weight The polyethylene used is ERTALENE HD 1000, CESTILENE MC (density 0.94, elasticity module of 650 MPa), conforming to ISO 5834/2 and NF S90-418 standards and/or polyethylene with a high molecular weight.

Cylindrical samples (pawns) and semi-spherical samples (cups) of polyethylene were submitted to an ionic implantation treatment with nitrogen, argon, oxygen, carbon and others, in an apparatus perfected and manufactured by UNIREC. (Robert LEVEQUE and Claude CHABROL, Application of ionic implantation in mechanical construction, Journées de GAMI, 8 and 9 March 1988, Paris).

The implantation energy was 80 keV.

2) Tests

Tests for friction between polyethylene parts and metal parts (stainless steel conforming to ISO 5832-I-NR S90-401 standards and titanium alloy conforming to ISO 5832-III-NF S90-405 standards) on two machines perfected and manufactured by Ecole Nationale Supérieure des Mines de Saint-Etienne.

One of these machines is a pawn-disk type, the other is a sphere-cup type. (A. PICHAT, J. RIEU, C. CHARBOL, A. RAMBERT, Effect of ionic implantation on the resistance to wear and fatigue of materials for orthopaedic use. Int. Symposium on wear-resistant materials, Bulletin du Cercle d'Etude des Métaux, 1987, 15-14, p 9-1).

The tests are carried out on orthopaedic-quality parts manufactured by the SERF company, in Décines.

The test conditions (stress, speed, environment) are similar to those for an artificial hip.

All the tests are carried out in an artificial physiological fluid (RINGER'S solution).

As an example, the results obtained on the stainless steel sphere—polyethylene cup couple are reported in FIGS. 1, 2, 3 and 4.

The curves show the variation of the torque (FIG. 1) and that of the wear rate of the polyethylene, expressed in loss of mass m (FIG. 2), as a function of the time t and the number of cycles N with:

1 couple comprising untreated PE/untreated 316L stainless steel 2 couple comprising untreated PE/316L stainless steel implanted with nitrogen 3 PE couple implanted with nitrogen/untreated 316L stainless steel 4 couple comprising PE implanted with nitrogen/316L stainless steel implanted with nitrogen.

These tests were stopped at one million cycles; however, longer tests enabled it to be verified that the beneficial effects of the implantation were retained.

These results highlight the fact that in the absence of any implantation, wear is significant and that in practice the implantation of the polyethylene alone is already sufficient to obtain a couple with significantly lower friction and rate of wear of the polyethylene (curve 3).

Figure 3:
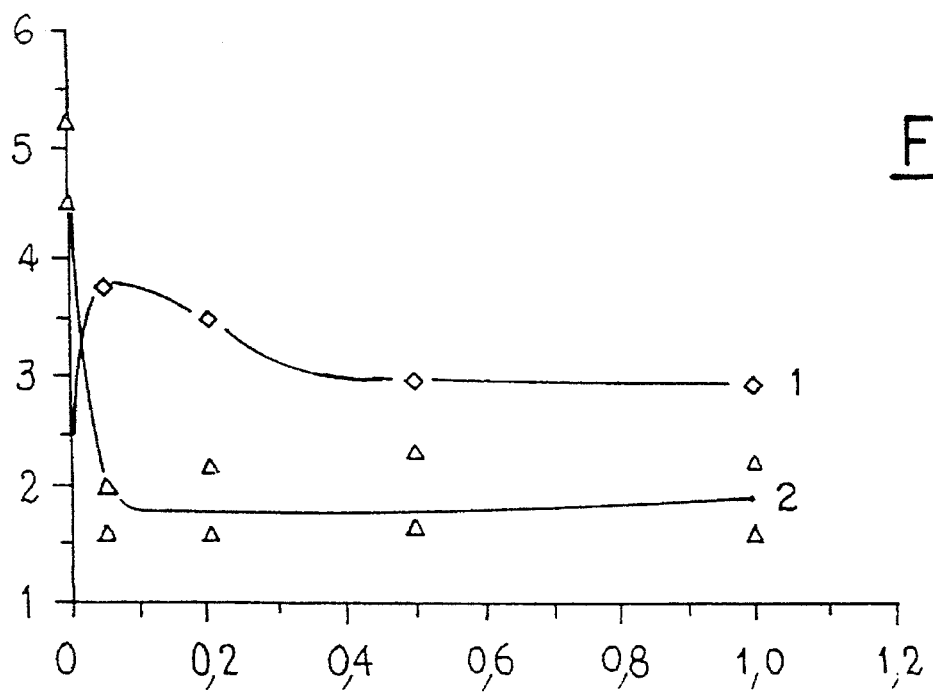
FIG. 3 is another graph of torque versus number of test cycles for various materials.
Figure 4:
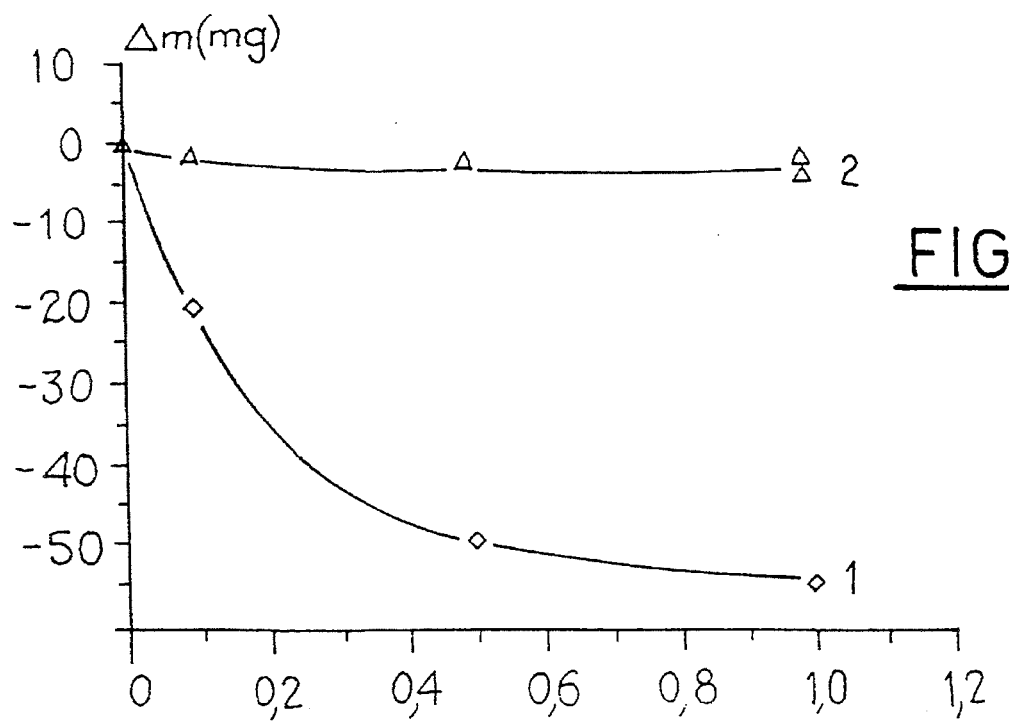
FIG. 4 is another graph of wear rate versus time for treated and untreated polyetheylene.

FIGS. 3 and 4 relate to the same tests of untreated 316L stainless steel spheres in comparison with polyethylene cups untreated or treated by implantation with argon ions. FIG. 3 shows that the torque is weaker when the polyethylene is implanted with argon (curve 2) than when it is not treated (curve 1, identical to curve 1 of FIG. 1).

Figure 2:
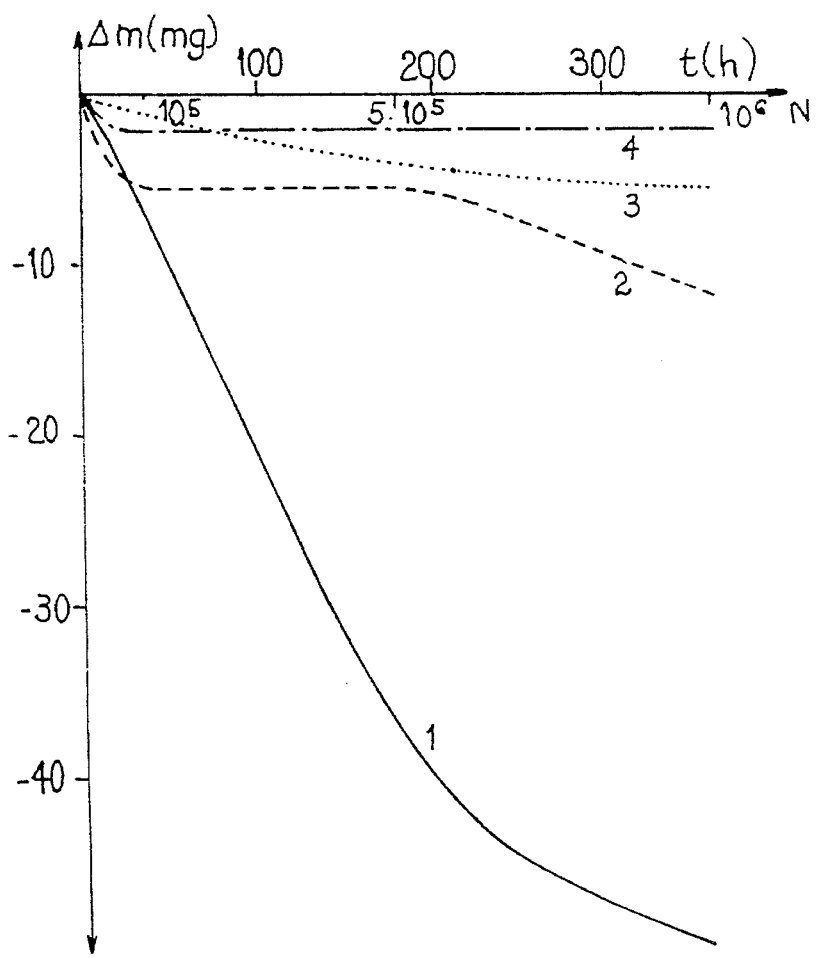
FIG. 2 is a graph of wear rate versus time for various polyethylene materials.

FIG. 4 shows that the rate of wear Δ m of the polyethylene is much less (5 mg as opposed to 50 mg) when the polyethylene is implanted with argon (curve 2) than when it is not treated (curve 1, identical to curve 1 of FIG. 2).

These results show that an ionic implantation of polyethylene with argon gives a decrease in the friction torque and a reduction in the rate of wear of the polyethylene in comparison to those obtained with an ionic implantation of polyethylene with nitrogen.

During the tests of ionic implantation with argon and nitrogen, a small quantity of carbon was introduced in an uncontrolled way which contributes to the results of the tests described above.

We claim:

1. A process for simultaneously reducing the coefficient of friction and the wear between a metal part and an organic polymer- or copolymer-based part, in an aqueous medium containing chlorides, comprising the step of:

submitting the organic polymer- or copolymer-based part to a surface treatment by ionic implantation of elements selected from the group consisting of nitrogen, argon, oxygen and carbon in an amount and under conditions sufficient to impart a reduced coefficient of friction and wear to the part as compared to an organic polymer- or copolymer-based part which is untreated.

2. Process according to claim 1, wherein the polymer is a polyethylene.

3. Process according to claim 1, wherein the implantation is carried out with an energy of 10 to 300 keV.

4. Process according to claim 3, wherein the implantation is carried out with an energy of 50 to 150 keV.

5. A process for simultaneously reducing the coefficient of friction and the wear between a metal part and a polyethylene-based part, in an aqueous medium containing chlorides, comprising the step of:

submitting the polyethylene-based part to a surface treatment of ionic implantation of elements selected from the group consisting of nitrogen, argon, oxygen and carbon in an amount and under conditions sufficient to impart a reduced coefficient of friction and wear to the part as compared to an organic polymer- or copolymer-based part which is untreated.

* * * * *